United States Patent [19]
Yamamura

[11] Patent Number: 4,486,777
[45] Date of Patent: Dec. 4, 1984

[54] DEFECT DETECTING APPARATUS AND METHOD

[75] Inventor: Tatsuo Yamamura, Hino, Japan

[73] Assignee: Fuji Electric Company, Ltd., Kanagawa, Japan

[21] Appl. No.: 432,408

[22] Filed: Sep. 30, 1982

[30] Foreign Application Priority Data

Oct. 14, 1981 [JP] Japan .................. 56-162725

[51] Int. Cl.³ .................. H04N 7/18
[52] U.S. Cl. .................. 358/106; 250/563; 364/507
[58] Field of Search .................. 358/106, 101, 107; 250/562, 563, 572; 364/507; 356/237

[56] References Cited

U.S. PATENT DOCUMENTS 4,207,593 6/1980 Deutsch .................. 358/106
4,364,113 12/1982 Sengebusch .................. 358/106

FOREIGN PATENT DOCUMENTS 52-83745 7/1977 Japan .
1417721 12/1975 United Kingdom .

Primary Examiner—Howard W. Britton
Attorney, Agent, or Firm—Spencer & Frank

[57] ABSTRACT

An apparatus and method for detecting defects in a substrate, including the periphery of the substrate, by the use of an image pickup device which sequentially scans the substrate along each of a plurality of vertically displaced horizontal lines for equal horizontal scanning periods. The analog output of the pickup device is coded to provide a binary coded signal having a polarity determined by the amount of light reflected from the substrate at each incremental portion of the scanning periods. The binary coded signal is shifted for a first interval which is less than the horizontal scanning period to obtain a first shifted output, and then further shifted for a second interval, measured from the end of the first interval, which is equal to the horizontal scanning period to obtain a second shifted output. The polarities of the first and second shifted outputs are compared in a comparator, the presence of a defect in the substrate being indicated when the first and second shifted outputs have predetermined opposite polarities at a given instant of time followed by a reversal in the polarities of each of the first and second shifted outputs.

7 Claims, 10 Drawing Figures

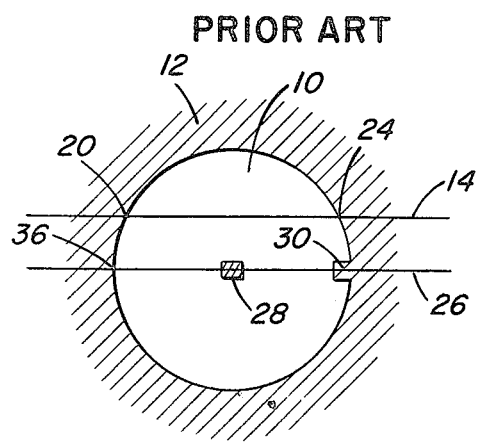
FIG. 1 PRIOR ART
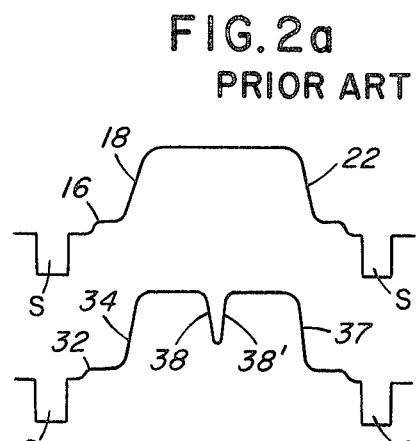
FIG. 2a PRIOR ART
FIG. 2b PRIOR ART
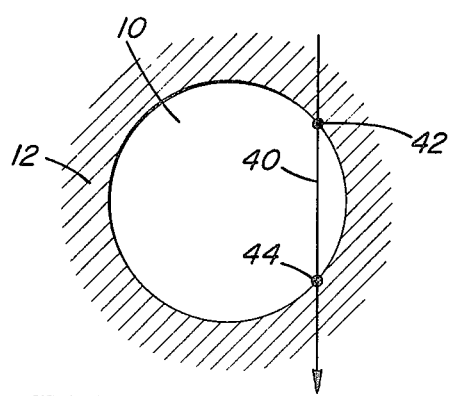
FIG. 3a
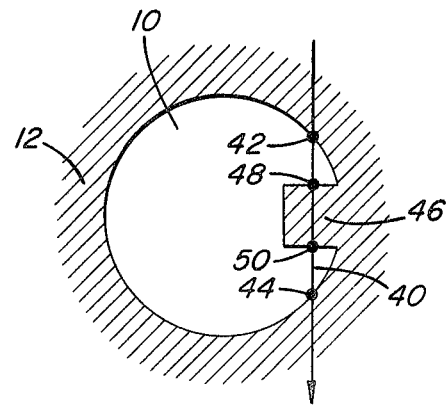
FIG. 3b
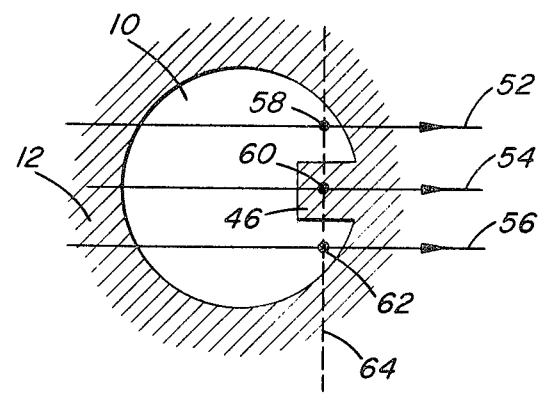
FIG. 3c

DEFECT DETECTING APPARATUS AND METHOD

BACKGROUND OF THE INVENTION

This invention relates to an apparatus and method for detecting defects in a substrate and, in particular, to the detection of defects located along the peripheral edge of the substrate by scanning with an image pickup device.

Semiconductor wafers and other substrates are subject to breakage, cracks and discoloration which can make them unsuitable for their intended use. A known method of testing substrates for such imperfections is to raster-scan the substrate with an image pickup device such as an industrial television camera. In this method, the image of the substrate on the photoelectric screen of the camera tube is scanned horizontally by an electron beam, line by line, until the entire substrate has been viewed. When so scanned, an electric current flows at the output of the pickup device which has an instantaneous magnitude proportional to the brightness of the portion of the image scanned. Defects are detected by observing a change in the output level of the pickup device as the substrate is scanned.

When a defect is located toward the center of the substrate, that is, away from its periphery, the change in the output level of the pickup device is relatively easy to detect. However, if the defect is at or close to the periphery or contour of the substrate, it can be quite difficult to distinguish the peripherial defect from the surrounding material by observing only the change in output level during horizontal scanning. Nevertheless, it is just as important to find peripheral defects as those located relatively far from the edge of the substrate.

A method for detecting a defect at the periphery of a circular sample is disclosed in a Japanese Patent Application No. 52-83745.

In accordance with this method, the coordinates of a standard substrate are stored in a memory and the coordinates of the sample to be tested for defects are conformed with those of the standard on a point-by-point basis. Any difference between the coordinates measured for the sample and the coordinates of the standard indicates that a defect is present in the sample. With this method, a large change in the contour can easily be detected but a small change is hard to detect. Consequently, the method is not suitable for the detection of small defects in the peripheral region of the sample and the method is influenced by a change in the size of the sample. Also, since the coordinates are compared one after the other, processing time is lengthy, and a memory is needed to store the coordinates which has the disadvantage of increased cost.

Accordingly, it is an object of the present invention to overcome the disadvantages of the prior art by providing a low-cost defect detecting apparatus and method which permits location of defects forming part of the contour or periphery of a substrate as well as defects located in the inner portion of the substrate. Other objects are to reduce the processing time so that the detection is completed simultaneously with the completion of the image pickup of one picture frame and eliminate the need for a memory to store coordinates.

SUMMARY OF THE INVENTION

In accordance with the present invention, an apparatus and method are provided for detecting defects in a substrate, including the periphery of the substrate, by the use of an image pickup device which sequentially scans the substrate along each of a plurality of vertically displaced horizontal lines for equal horizontal scanning periods. The analog output of the pickup device is coded to provide a binary coded signal having a polarity determined by the amount of light reflected from the substrate at each incremental portion of a scanning period. The binary coded signal is shifted for a first interval which is less than the horizontal scanning period to obtain a first shifted output, and then further shifted for a second interval, measured from the end of the first interval, which is equal to the horizontal scanning period to obtain a second shifted output. The polarities of the first and second shifted outputs are compared in a comparator, the presence of a defect in the substrate being indicated when the first and second shifted outputs have predetermined opposite polarities at a given instant of time followed by a reversal in the polarities of each of the first and second shifted outputs.

BRIEF DESCRIPTION OF THE DRAWINGS

FIG. 1 is an illustration of a substrate showing how a prior art defect detection device operates.

FIGS. 2a and 2b are diagrams showing the video wave forms generated by a camera scanning the substrate of FIG. 1.

FIGS. 3a, 3b and 3c illustrate the operation of the present invention.

DESCRIPTION OF THE PREFERRED EMBODIMENTS

Figure 4:
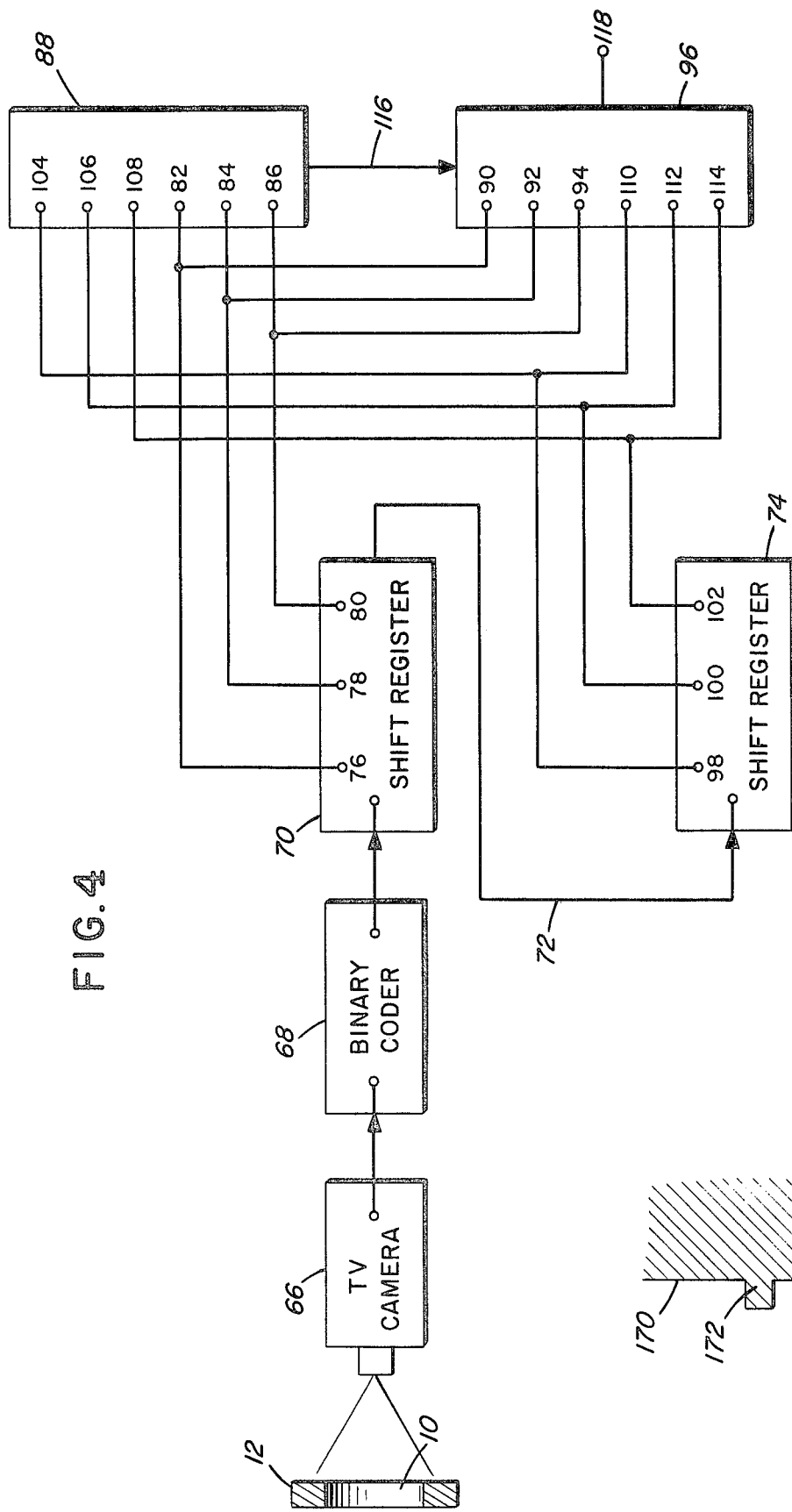
FIG. 4 is a block diagram showing one embodiment of the present invention.

FIG. 1 illustrates a known method of detecting defects in a substrate 10. In this method, the substrate is scanned by an image pickup device, such as a television camera, and the changes in the output level of the pickup device along the scanning line noted as it passes from the region 12 surrounding the substrate to the substrate itself. Changes in output level are also observed as the camera scans from a region of the substrate which has no defects to one which contains a defect.

In FIG. 1, scanning line 14 traverses a region in which no defects are present and therefore the video waveform 16 at the output of the pickup device is as shown in FIG. 2a. In FIG. 2a, synchronizing pulses are indicated at S, the increase in pickup output at the point 20 of FIG. 1 where the camera moves across the boundary from the region 12 outside the substrate to the substrate 10 is shown at 18 and the decrease in pickup output as the camera moves across the boundary 24 from the substrate 10 to the surrounding region 12 is indicated at point 22. Portions 18 and 22 of the waveform 16 represent conversion points corresponding respectively to a change from a relatively small amount of reflected light in the region 12 to a larger amount of reflected light in the substrate region 10, and from a relatively large amount of reflected light in the region 10 to a smaller amount of reflected light in the region 12.

Line 26 in FIG. 1 is a scanning line which traverses two defects 28 and 30 in the substrate 10. Referring to FIG. 2b, the waveform 32 shows the output of the pickup device including the synchronizing pulses S and the conversion point 34 from low to high output when the pickup scans along line 26 from region 12 to region 10 at the boundary point 36. When the pickup traverses the defect 28, the light reflected from the substrate is initially reduced and then increased, and there is a corresponding reduction in camera output followed by an increase, as shown at 38 and 38' respectively in FIG. 2b, making it possible to detect the defect 28. However, when the pickup scans the portion of substrate 10 where the defect 30 abuts region 12, defect 30 is difficult to detect because the change which it produces in the reflected light merges with the change in reflected light picked up by the camera as it traverses the boundary between the substrate 10 and region 12.

Thus, two changes in light output would be measured along line 14 at the boundary points 20 and 24 indicating that there are no defects in this part of the substrate. On the other hand, four changes in light output at 34, 38, 38' and 37 would be measured along line 26 indicating that one defect is present, although an additional undetected defect 30 is actually present. Further, if defect 28 had not been present along line 26, the number of light changes for line 26 would have been the same as for line 14, and again the presence of defect 30 would have gone undetected.

FIGS. 3a, 3b and 3c illustrate the operation of the present invention. In FIG. 3a, the substrate 10 has no defects and is scanned vertically along line 40 in the direction of the arrow. A change in light output from shade to light is detected at the boundary point 42 and a change in light output from light to shade at the boundary point 44. In FIG. 3b, the presence of a defect 46 along the periphery of the substrate is detected because a change in light output occurs at point 48 from light to shade and at point 50 from shade to light, in addition to the changes from shade to light at peripheral point 42 and from light to shade at peripheral point 44. Thus, the direction of change in the level of light output at points 48 and 50 caused by the defect is opposite to that occurring at the peripheral points 42 and 44 respectively making it possible to easily detect the peripheral defect 46.

Examination of substrates for defects is generally carried out by horizontal raster scanning rather than vertical scanning, as depicted in FIGS. 3a and 3b. Accordingly, this invention provides a method and apparatus for detecting defects in a substrate, including peripheral defects, by horizontal scanning.

Referring to FIG. 3c, the substrate 10 is scanned along a first horizontal line 52 followed by scanning along a second horizontal line 54 through peripheral defect 46 and a third horizontal line 56. Output level changes are detected and compared for vertically displaced-picture elements at, for example, points 58, 60 and 62 respectively, which are located on a vertical line 64. The number of picture elements in the region to be compared can be selected as a function of the size of the defect to be detected, as discussed hereinafter.

FIG. 4 is a block diagram of an apparatus for carrying out the defect detection method illustrated by FIG. 3c. In FIG. 4, an analog video signal is generated at the output of a television camera 66 which scans the substrate 10 and is impressed on the input of a binary coder 68. This signal is converted to a binary coded signal in the binary coder 68 and coupled to the input of a first shift register 70 which has a data shift capacity corresponding to the time required for one horizontal line to be scanned. The output of shift register 70 is coupled by a line 72 to a second shift register 74 having the same capacity as shift register 70. Shift register 70 is provided with output terminals 76, 78 and 80 for extracting data from the shift register which is then fed to input terminals 82, 84 and 86 respectively of a comparator 88 and terminals 90, 92 and 94 respectively of a comparator 96. Data from shift positions corresponding to those at terminals 76, 78 and 80 of register 70 are extracted from output terminals 98, 100 and 102 respectively of register 74 and applied to terminals 104, 106 and 108 respectively of comparator 88 and terminals 110, 112 and 114 respectively of comparator 96. A signal appears at terminal 98 of register 70 one horizontal scanning period after the same signal has appeared at terminal 76 of register 70. Similarly, signals appear at terminals 100 and 102 of register 74 one horizontal scanning period after they have appeared at terminal 78 and 80 respectively of register 70. Comparator 88 is coupled by a connection 116 to comparator 96 and a defect indicating an output is obtained at output terminal 118 of comparator 96.

In operation, the analog signal from television camera 66 which sequentially scans the substrate 10 along horizontal lines 52, 54 and 56 of FIG. 3 is compared in binary coder 68 with a predetermined threshold value and the resulting binary signal applied to the input of register 70. In register 70, which has a data shift capacity of one horizontal scanning period, the data is shifted and then input to register 74 where it is again shifted. Data is fetched from corresponding shift positions of the two registers and compared in comparators 88 and 96. Referring to FIG. 3c, the comparison includes the light output levels corresponding to up to a three-picture element at the region surrounding point 58 on line 52, the levels corresponding to up to a three-picture element at point 60 surrounding the defect 46 on line 54 and the light output levels of a three-picture element surrounding point 62.

In the comparator 88, data at terminals 76, 78 and 80 for a three-picture element from shift register 70 is compared with data at terminals 98, 100 and 102 for a three-picture element from shift register 74. When the corresponding outputs of the registers are at different levels, for example corresponding to light and shade, comparator 88 generates an output signal on line 116 which starts the comparator 96. In comparator 96, after an interval equal to one horizontal scanning period measured from the instant of comparison in comparator 88, the data for a three-picture element from shift register 70 is compared with the data for a three-picture element from shift register 74.

Referring again to FIG. 3c, this latter comparison may correspond to a level comparison between a horizontal three-picture element located at the region 60 on the scanning line 54 and a horizontal three-picture element located at the region 62 on the scanning line 56. Consequently, if the difference in signal level between the two signals is, for example, from shade to light, the comparator 96 will generate a signal at terminal 118 which indicates the presence of the defect 46 in the region 60.

In this description, a three-picture element is used as a unit of level comparison. However, it will be understood, particularly in connection with the discussion of FIG. 5 hereinafter, that an arbitrary number of picture elements may be used for level comparison depending upon the size of the defect to be detected.

Figure 5:
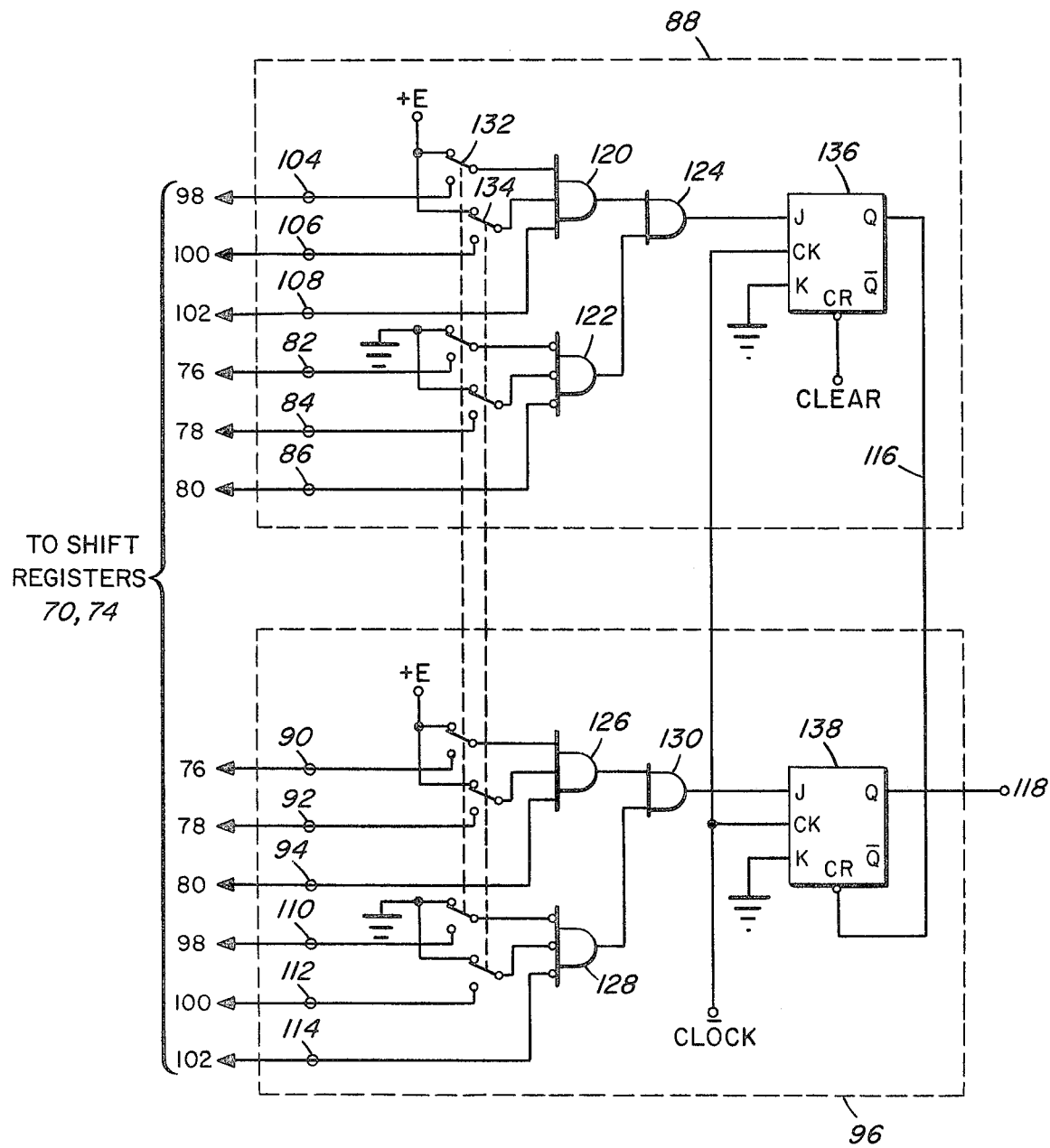
FIG. 5 is a schematic diagram showing the circuits of the comparators used in FIG. 4.

FIG. 5 is a schematic diagram illustrating the circuits of comparator 88 and 96 of FIG. 4. In order to facilitate understanding of the invention, the numbers of the terminals on shift registers 70 and 74 which are connected to the input terminals of the comparator 88 and 96 are shown on FIG. 5. Comparator 88 is provided with an AND gate 120 and a NOR gate 122 having their outputs connected to the input of an AND gate 124. Similarly, comparator 96 is provided with an AND gate 126 and a NOR gate 128 having their outputs connected to the input of an AND gate 130. One input of each of AND gates 120 and 126 is connected to comparator input terminals 108 and 94 respectively, and one input of each of NOR gates 122 and 128 is connected to comparator input terminals 86 and 114 respectively. A second input of each of AND gates 120 and 126 is connected through contacts of a first interlocked switch 132 to either terminals 104 and 90 respectively or to a source of positive voltage +E. A second input of each of NOR gates 122 and 128 is connected through contacts of interlocked switch 132 to either terminals 82 and 110 respectively or ground. A third input of each of AND gates 120 and 126 is connected through contacts of a second interlocked switch 134 to either terminals 106 and 92 respectively or the source of positive voltage +E, and a third input of each of NOR gates 122 and 128 is connected through contacts of interlocked switch 134 to either terminals 84 and 112 respectively or ground.

The outputs of AND gates 124 and 130 are coupled to the J inputs of JK flip-flops 136 and 138 respectively. The K inputs of flip-flops 136 and 138 are grounded, their CK inputs connected to a clock and the Q output of flip-flop 136 coupled by connection 116 to the CR input of flipflop 138. The Q output of flip-flop 138 is connected to the output terminal 118.

Assume that a light area is represented at the output of binary coder 68 by a logic 1 and a shaded or darker area by a logic 0. Assume further that the switches 132 and 134 are placed in the opposite position from that shown in FIG. 5 whereby the terminals 104, 106 and 108 are connected to the three inputs of AND gate 120, terminals 82, 84 and 86 to the three inputs of NOR gate 122, terminals 90, 92 and 94 to the three inputs of AND gate 126 and terminals 110, 112 and 114 to the input of NOR gate 128.

When logic 0's appear at the output terminals 76, 78 and 80 of shift register 70 and logic 1's at the output terminals 98, 100 and 102 of shift register 74, terminals 82, 84, and 86 of the comparator 88 are all driven to logic 0's and terminals 104, 106 and 108 to logic 1's. Consequently, the outputs of AND gate 120 and NOR gate 122 are both at 1, the output of AND gate 124 is also 1 and the Q output of JK flip-flop 136 becomes 1. This indicates that a region has been found on substrate 10 where there is a change from a light to a shade portion, with the possible presence of a defect in the substrate. The output of flip-flop 136 is coupled by lead 116 to the terminal CR of flip-flop 138 thereby causing flip-flop 138 to be set.

After one horizontal scanning period has elapsed, assume that the output terminals 76, 78 and 80 of shift register 70 are at logic 1's and the terminals 98, 100 and 102 at logic 0's, that is, the logic 0's at terminals 76, 78 and 80 one horizontal scanning period earlier have been shifted to terminals 98, 100 and 102 and the camera scanning line 56 of FIG. 3c has not encountered a defect at point 62. Accordingly, the outputs of AND gate 126 and NOR gate 128 are at 1, the output of AND gate 130 is at 1 and flip-flop 138 is set thereby producing an output at terminal 118. The appearance of a signal at terminal 118 means that along vertical line 64 of FIG. 3c there was a change from a light portion (point 58) to a shaded portion (point 60) to a light portion (point 62) indicating that a defect is present at point 60.

When both switches 132 and 134 are placed in the position shown in FIG. 5, the inputs to AND gates 120, 126 and NOR gates 122, 128 are controlled only by signals at terminals 108, 94, 86 and 114 respectively, the signals on terminals 108 and 114 being generated at terminal 102 of shift register 74 and the signal at terminals 94 and 86 being generated at terminal 80 of shift register 70. This occurs because the remaining AND gate input terminals are at the +E position and the remaining NOR gate inputs are grounded. With the switches 132 and 134 in the positions shown in FIG. 5, a defect only one-picture element in size will be detected even though the defect is close to the periphery of the substrate as in FIG. 3c.

If switch 132 is switched to the lower position but switch 134 is left in the position shown in FIG. 5, comparator terminals 104, 82, 90 and 110 are connected to the inputs of AND gate 120, NOR gate 122, AND gate 126 and NOR gate 128 respectively. Consequently, defects which are equivalent to two-picture elements will be detected. The apparatus will also detect defects having a width of two-picture elements when switch 134 is switched to the lower position and switch 132 remains in the position shown in FIG. 5.

Accordingly, the detection sensitivity of the apparatus can be controlled by setting switches 132 and 134 to detect defects which are, two or three-picture element in size. Further, by the use of additional shift register outputs and switching stages the sensitivity can be reduced still further to detect only defects having still larger horizontal dimensions.

It is apparent that since the subject detection system employs changes between light and shade conditions based on data which is vertically arranged to detect a defect, the defect will be detected in a circular substrate in the same manner regardless of whether it is in the peripheral or interior portions of the substrate.

Figure 6:
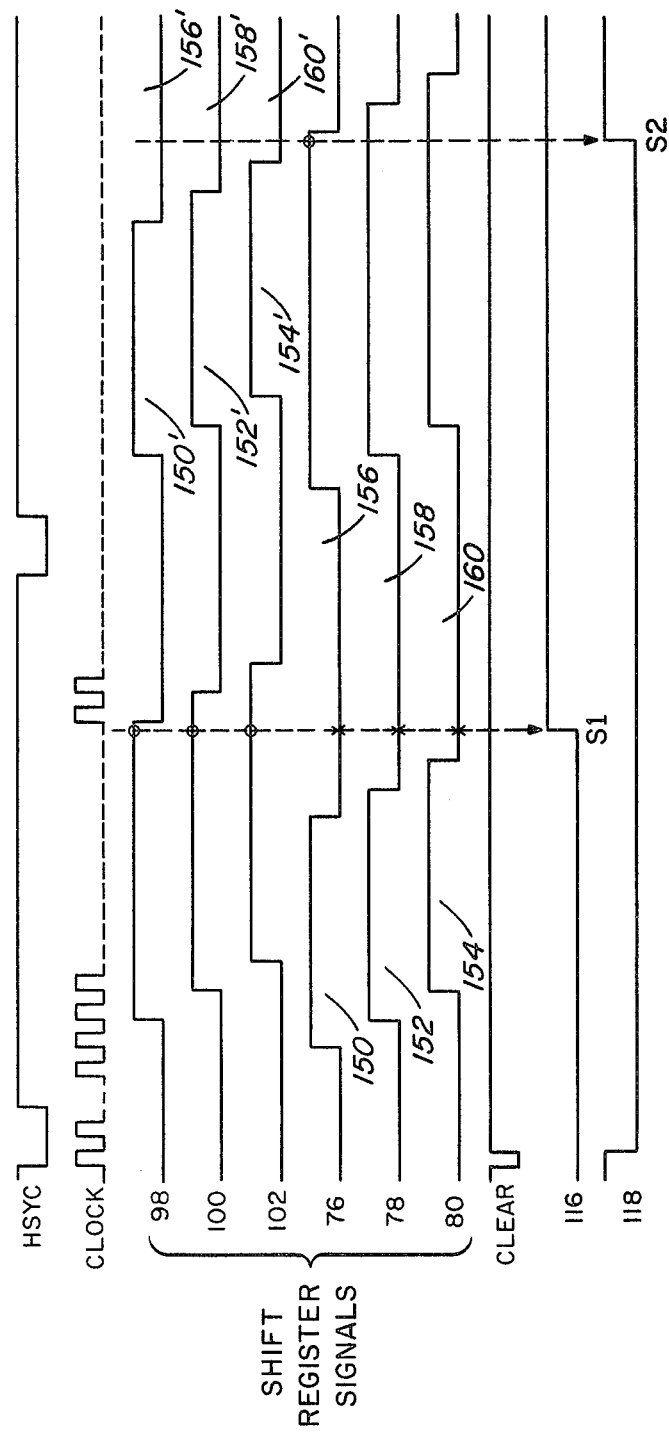
FIG. 6 is a timing chart showing signals present in the comparator of FIG. 5.

FIG. 6 is a timing chart for the signals in the system of FIG. 4 wherein the signals at the outputs of the shift registers 70 and 74 are identified by their terminal numbers, the signal coupled from comparator 88 to comparator 96 by the lead designation 116 and the output of comparator 96 by the output terminal number 118. HSYC is the synchronizing signal for horizontal scanning of the television camera, the image pickup picture being sequentially scanned from the upper to the lower side of the substrate synchronously with this signal. CLOCK is a fixed cycle timing signal which is applied to the shift registers 70, 72 to synchronously and sequentially shift the binary coded data applied to the input of shift register 70 by the binary coder 68, the CLOCK signal also being applied to flip-flops 136 and 138 as shown in FIG. 5. The CLEAR signal is applied to the CR terminal of JK flip-flop 136 to clear the circuit after each defect has been detected.

In FIG. 6, the register 70 output signals at terminals 76, 78 and 80 occur sequentially at one clock pulse intervals. The portion of the substrate 10 being scanned is free of defects when the signals have a value of 1 as at 150, 152 and 154 and may have a defect when the signal is 0 as at 156, 158 and 160. The outputs 98, 100 and 102 of shift register 74 from the previous horizontal scan all have a value of 1 at the instant $S_1$ when the outputs at terminals 76, 78 and 80 are 0, and therefore the JK flip-flop 136 is switched from a 0 output at terminal Q to a 1, as previously explained. The operating mode of FIG. 6 is obtained with both switches 132 and 134 switched from the position shown in FIG. 5 so that defects having a size of at least three picture elements are detected.

During the next line scan, the signal represented by 50 and 156 is coupled to shift register 74 where it is taken from output terminal 98 as shown at 150' and 156'. Similarly, the signals corresponding to 152, 158 and 154, 160 are shifted in time as shown at 152', 158' and 154', 160'. At the instant $S_2$, terminals 98, 100 and 102 are all at 0 and terminals 76, 78 and 80 are all at 1 causing the JK flip flop 138 to generate a defect signal, that is a 1, at output terminal 118, in the manner already discussed in connection with FIG. 5.

In accordance with the present invention, a defect adjoining the periphery of a circular substrate can be detected since comparisons are made along vertical lines as the substrate is scanned horizontally. That is, changes between light and shade in the vertical direction are detected. Further, defects away from the periphery of the substrate are also detected by the disclosed system. With regard to processing time, signal processing is accomplished by shifting data for only one horizontal scanning period and therefore an image pickup period of one picture is adequate.

Since it is not necessary when employing the present invention to determine the external coordinates of the sample, changes in its size by enlargement or reduction, or movement of the sample within the camera picture will not effect the determination of defects.

Figure 7:
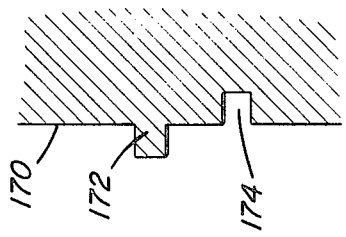
FIG. 7 illustrates the use of the invention to detect a defect in a substrate having a linear contour.

The method and apparatus can also be employed to establish the presence of defects in an elliptical sample if the sample is symmetrical and defined by a convex curve. A sample having a linear contour 170 in the vertical direction is shown in FIG. 7. It can be checked for unevenness, as represented by regions 172 and 174. In the case of convex defects, the black and white portions of the picture are inverted so that the convex area appears to be concave. Therefore, such a defect can also be detected by this invention.

It will be understood that the above description of the present invention is susceptible to various modifications, changes and adaptations, and the same are intended to be comprehended within the meaning and range of equivalents of the appended claims.

What is claimed is:

1. Defect detecting apparatus for detecting a defect in a substrate including a defect at the periphery thereof, said substrate being sequentially scanned by an image pickup device along each of a plurality of vertically displaced horizontal lines for equal horizontal scanning periods, comprising:

binary coder means coupled to the output of said image pickup device, said binary coder means converting the output of said image pickup device to a binary coded signal having a polarity determined by the amount of light reflected from said substrate at each incremental portion of said scanning periods;

signal shifting means for shifting said binary coded signal for a first interval which is less than said horizontal scanning period to obtain a first shifted output;

further signal shifting means for shifting said coded binary signal for a second interval, measured from the end of said first interval, which is equal to said horizontal scanning period to obtain a second shifted output; and comparator means for comparing the polarities of said first and second shifted outputs, the presence of a defect in said substrate being indicated when said first and second shifted outputs have predetermined opposite polarities at a given instant of time followed by a reversal in the polarities of each of said first and second shifted outputs.

2. Defect detecting apparatus for detecting a defect in a substrate including a defect at the periphery thereof, said substrate being sequentially scanned by an image pickup device along each of a plurality of vertically displaced horizontal lines for equal horizontal scanning periods, comprising:

a binary coder coupled to the output of said image pickup device, said binary coder converting the output of said image pickup device to a binary coded signal having a polarity determined by the amount of light reflected from said substrate at each incremental portion of said scanning periods;

a first shift register having an input coupled to the output of said binary coder and at least first and second outputs, the signal at said first output being delayed with respect to the signal at the input of said first shift register for an interval equal to said horizontal scanning period and the signal at said second output being delayed with respect to the signal at the input of said first shift register for a fixed interval less than said horizontal scanning period;

a second shift register having an input coupled to the first output of said first shift register and at least a first output, the signal at the first output of said second shift register being delayed with respect to the signal at the input of said second shift register for a fixed interval equal to the fixed interval by which the second output of said first shift register is delayed with respect to the input of said first shift register;

a first comparator having at least first and second inputs coupled to the first output of said second shift register and the second output of said first shift register respectively, said first comparator generating a signal at the output thereof when the signals at its first and second inputs are of predetermined opposite polarities; and a second comparator having at least first and second inputs coupled to the first output of said second shift register and to the second output of said first shift register respectively, said second comparator further having a third input coupled to the output of said first comparator, said second comparator generating a signal at the output thereof after generation of a signal at the output of said first comparator and when the signals at its first and second inputs are of polarities opposite the polarities of the first and second inputs respectively of said first comparator which caused generation of the output signal of said first comparator, generation of a signal at the output of said second comparator indicating the presence of a defect in said substrate.

3. A defect detecting apparatus as defined in claim 2 wherein said first shift register has at least one additional output delayed for a different specific interval than the second output of said first shift register and less than said horizontal scanning period, said second shift register has a corresponding additional output delayed for a specific interval equal to the delay of the corresponding additional output of said first shift register, and said first and second comparators have additional inputs coupled to the additional outputs of said first and second shift registers.

4. A defect detecting apparatus as defined in claim 2 wherein each of said first and second comparators comprises first and second AND gates, a NOR gate and a flip-flop, the outputs of the first AND gate and the NOR gate being coupled to the input of the second AND gate, the output of the second AND gate being coupled to the input of the flip-flop, the output of the flip-flop of the first comparator being coupled to the set input of the flip-flop in said second comparator and the output of said second flip-flop generating the output signal of said second comparator; and wherein the second output of said first shift register is coupled to the input of the NOR gate of said first comparator and the first AND gate of said second comparator, and the first output of said second shift register is coupled to the input of the first AND gate of said first comparator and the NOR gate of said second comparator.

5. A defect detecting apparatus as defined in claim 3 wherein each of said first and second comparators comprises first and second AND gates, a NOR gate and a flip-flop, the outputs of the first AND gate and the NOR gate being coupled to the input of the second AND gate, the output of the second AND gate being coupled to the input of the flip-flop, the output of the flip-flop of the first comparator being coupled to the set input of the flip-flop in said second comparator and the output of said second flip-flop generating the output signal of said second comparator; and additional outputs of said first shift register are coupled to the input of the NOR gate of said first comparator and the first AND gate of second comparator, and the first and additional outputs of said second shift register are coupled to the input of the first AND gate of said first comparator and the NOR gate of said second comparator.

6. A defect detecting apparatus as defined in claim 5 which further comprises switching means interposed between the outputs of said first and second shift registers and the inputs of said first AND and NOR gates for switching selected outputs of said shift registers to the inputs of said gates, said switching means determining the resolution of said defect detecting apparatus.

7. A method of detecting a defect in a substrate including a defect at the periphery thereof including the steps of:
   scanning a substrate by means of an image pickup device along each of a plurality of vertically displaced horizontal lines for equal horizontal scanning periods, said pickup device generating a signal having an amplitude determined by the amount of light reflected by said substrate;
   converting the output of said image pickup device to a binary coded signal, said binary coded signal having a polarity determined by the amount of light reflected from said substrate at each incremental portion of said scanning periods;
   shifting said binary coded signal for a first interval which is less than said horizontal scanning period to obtain a first shifted output;
   further shifting said binary coded signal for a second interval, measured from the end of said first interval, which is equal to said horizontal scanning period to obtain a second shifted output; and
   comparing the polarities of said first and second shifted outputs, the presence of a defect in said substrate being indicated when said first and second shifted outputs have predetermined opposite polarities at a given instant of time followed by a reversal in the polarities of each of said first and second outputs.

* * * * *